United States Patent [19]

Halbreich et al.

[11] Patent Number: 6,150,181
[45] Date of Patent: Nov. 21, 2000

[54] MAGNETIC NANOPARTICLES COUPLED TO ANNEXINE, AND UTILIZATION THEREOF

[75] Inventors: Avraham Halbreich, Puteaux; Domagoj Sabolovic, Paris; Claude Sestier, Montreuil; Danielle Geldwerth; Jean-Noël Pons, both of Paris; Jacky Roger, Villecresnes, all of France

[73] Assignee: Universite Pierre et Marie Curie, Paris, France

[21] Appl. No.: 08/981,239

[22] PCT Filed: Jun. 20, 1996

[86] PCT No.: PCT/FR96/00964

§ 371 Date: Jun. 11, 1998

§ 102(e) Date: Jun. 11, 1998

[87] PCT Pub. No.: WO97/01760

PCT Pub. Date: Jan. 16, 1997

[30] Foreign Application Priority Data

Jun. 29, 1995 [FR] France .................................. 95 07865

[51] Int. Cl.⁷ .......................... G01N 33/553; G01N 15/06
[52] U.S. Cl. .......................... 436/526; 436/518; 436/535; 436/538; 436/823; 422/50; 422/55; 422/57; 422/63; 422/68.1; 422/186.01; 422/255; 422/261; 435/4; 435/7.1; 428/402; 428/403; 427/2.11; 427/2.13; 427/2.14; 427/216; 427/331; 427/337; 427/338
[58] Field of Search .................................. 438/526, 518, 438/535, 538, 823; 422/50, 55, 57, 63, 68.1, 186.01, 255, 261; 435/4, 7.1; 428/402, 403; 427/2.11, 2.13, 2.14, 216, 331, 337, 338

[56] References Cited

U.S. PATENT DOCUMENTS 4,920,061  4/1990  Poynton et al. ......................... 436/526
5,264,157  11/1993 Bidan et al. ............................. 252/519
5,384,073  1/1995  Shigekawa et al. ................. 252/313.1
5,514,340  5/1996  Landsdorp et al. ..................... 422/101
5,610,274  3/1997  Wong ...................................... 530/334
5,627,036  5/1997  Reutelingsperger ................... 435/7.21
5,817,292  10/1998 Snow et al. ........................... 424/9.323

FOREIGN PATENT DOCUMENTS 2662539   11/1991  France .
10 40 817  7/1991  Germany .
2244987   12/1981  United Kingdom .

OTHER PUBLICATIONS

Claude Sestier, et al., "Use of annexin V–ferrofluid to enumerate ertythrocytes damaged in various pathologies or during storage in vitro", Nov. 1, 1995, C.R. Acad. Sci. Paris, Sciences de la vie/Life sciences, 1995; vol. 318, No. 11, pp. 1141–1146.

Primary Examiner—Christopher L. Chin
Assistant Examiner—Pensee T. Do
Attorney, Agent, or Firm—Venable; Michael A. Gollin; Charles C. Rories

[57] ABSTRACT

The invention relates to a process for producing ferrofluid-forming magnetic particles substituted by DMSA (FFSH) that can be covalently coupled, directly or through a difunctional reactant, to an effector, which process comprises combining DMSA with ferrofluid-forming magnetic particles to form FFSS particles having disulfide bonds, and reducing the disulfide bonds of the FFSS at basic pH to form FFSH. The invention includes a composition comprising such FFSH magnetic particles. The invention also relates to a method in which FFSH magnetic particles are incubated with an effector comprising at least one functional group which forms an S—S, C—S, C—C, or C—N bond with DMSA, so that a covalent effector-FFSH complex is formed. The invention further includes a method for separating and/or distinguishing between molecules or cells having a ligand that forms an affinity complex with an effector-FFSH particle of the invention, and those molecules or cells that do not have such a ligand.

19 Claims, 5 Drawing Sheets

MAGNETIC NANOPARTICLES COUPLED TO ANNEXINE, AND UTILIZATION THEREOF

FIELD OF THE INVENTION

The present invention relates to a new means making it possible to differentiate and/or separate components of a complex mixture, especially cells, still more particularly red corpuscles, and exhibiting at their surface a receptor specific for an effector coupled to magnetic particles. The surface complexing of the particles by dimercaptosuccinic acid (DMSA) of formula HOOC—CHSH—CHSH—COOH makes it possible to obtain a ferrofluid which is stable in aqueous medium. The invention also relates to an improvement to the process for preparation of these DMSA-treated ferrofluids, making the latter capable of being employed in a process of differentiation or of separation of cells or of molecules.

In what follows, the term "effector" or "ligand" means any molecule or macromolecule that is free or bonded to a structure which contains it or which carries it, and capable of directly or indirectly forming an affinity complex with another molecule or macromolecule.

Also in what follows the numbers within brackets refer to the literature references at the end of the description.

BACKGROUND OF THE INVENTION

Biomedical applications of colloidal solutions of magnetic particles, or ferrofluids, have developed essentially in three directions:

imaging (MRI) as contrast agents (1, 2, 3), magnetic separation of various cells, organites or biological molecules (4, 5, 6, 7, 8, 9)

destruction of target cells by creation of a local hyperthermia under pulsating magnetic field (10).

The most extensively employed magnetic particles are the ferrites $MFe_2O_4$ (including magnetite $Fe_3O_4$) and maghemite $\gamma\ Fe_2O_3$. The surface of the particles must be conditioned in order to obtain colloidal solutions that are stable in physiological medium. In most cases the particles are coated with macromolecules such as carbohydrates like dextran (10, 12, 1), proteins like albumin (5, 8) or synthetic polymers like methacrylates and organosilanes (7, 9, 13). However, as Groman indicates, covering the particles with macromolecules of high molecular mass does not make it possible to obtain sols that are stable in the long term. The macromolecules separate from the particles, which then gradually aggregate. Other methods of conditioning the surface of the particles have been proposed, such as the use of molecules of low molecular mass, containing complexing groups such as phosphates, phosponates and carboxylates (2). Very particularly, hydroxylated polycarboxylic acids such as citric and tartaric acids and polycarboxylic acids containing thiol groups, like dimercaptosuccinic acid (DMSA) are complexed with the surface atoms of iron(III) (14). Each of these complexing molecules is bonded to one or more surface sites of the particles. The aqueous sols thus obtained are very stable in physiological conditions.

In many biomedical applications of the magnetic particles the latter must be coupled to a specific protein. Thus, in the case of cell sorting under magnetic field the particles must be capable of bonding specifically to the target cells. This recognition is often ensured by the formation of an antigen-antibody complex between a surface antigen of the target cell and an antibody bonded to the particles. The protein may be either adsorbed directly at the surface of the particles (4) or bonded covalently (5, 7, 13). The use of difunctional intermediate compounds such as N-succinimidyl 3-(2-pyridyldithio)propionate (SPDP) (8, 14) makes it possible to bond an antibody strongly to a particle via a peptide bond and a disulfide bridge, without damage to the protein or to its antigenic properties (15).

French patent No. 2 662 539 (14) described a process for obtaining finely divided magnetic supports by controlled modification of particles filled with precursor ferrofluid, including a stage of treatment with an agent capable of modifying the nature of the surface of the said particles, and so as to make them stable in polar or nonpolar solvents in wide pH ranges and to endow them with a chemical or biological reactivity. An example of such a modification is a DMSA-based ferrofluid making it possible to render thiol groups available and reactive at the surface of these so-called substituted ferrofluids; however, in the usual pH and ionic strength conditions, these thiol groups tend to become oxidized and to form disulfide bridges making these ferrofluids ill-suited to a use as constituents of a magnetic effector.

A use, especially for differentiating and/or separating cells which have at their surface a receptor for a ligand signaling a property or a particular physiological state, made it necessary to improve the ferrofluids of patent 2 662 539 (14) in such a way that disulfide bridges do not limit the coupling; Such an improvement then making it possible to produce DMSA ferrofluid complexes coupled covalently to the said effectors and then to employ them as means for differentiating and separating complexes or cells carrying, if appropriate, the receptor for the said effector.

The effector/receptor affinity pairs are numerous and the invention as described below will be capable of being easily applied by a person skilled in the art to the pairs of receptors of interest to him/her, as well as to other affinity pairs such as antibody/antigen, lectin/polysaccharide, biotin/avidin and nucleic acid (+ and − strands) pairs and the like, as soon as the effector can be coupled to the particles through the intermediacy of a difunctional reactant optionally comprising thiol residues one of the functional groups of which permits the bonding to the effector and the other functional group of which is capable of forming S—S, C—S, C—C or C—N bonds with DMSA.

A particular application of the use of the ferrofluid coupled to an effector is the use as effector of an annexine, like annexine V, which has a particular affinity, in the presence of calcium ions, for anionic phospholipids, like phosphatidylserine (PS) and in, a lesser degree, phosphatidylethanolamine (PE). These compounds of the plasmic membranes are essentially localized in the inner layer of the membranes, in contrast to other phosphatidylcholine and sphingo-myelin type compounds which are, on the contrary, predominantly localized in the outer layer of the plasmic membranes. The cell membranes exhibit an asymmetry such that, when the membrane is healthy, the phosphatidylserines and some of the phosphatidyl-ethanolemines residing on the inner layer are inaccessible, whereas, when the membranes are perturbed, there is a random localization of these same phospholipids. Consequently, those that are localized in the inner layer of the membranes become accessible over the whole cells and, in particular, phosphatidyl-serine becomes accessible to a coupling by an annexine like annexine V or capable of being attacked by an external phospholipase. This perturbation may be due to an inflammation, to an apoptosis (16), to autoimmune reactions (17), to a sickle cell anemia (18, 19), or to a pathological or infectious state of the individual (19, 22), or simply to an excessive aging of the cells and especially of the blood cells during their storage in vitro (23). It is thought that the presence of phosphatidylserine in the outer layer of the plasmatic membrane constitutes a signal for the elimination of the cell by the immune system (24, 25).

Patent application WO 91/09628 relates to the use of anticoagulant polypeptides of the annexine class which are provided with a marker and these marked annexines or VAC (vascular anticoagulant protein) are employed as means for differentiating phosphatidyl-serines from phosphatidylcholines and for thus diagnosing a prethrombotic state via the presence of a coupling of annexine to the cells exhibiting a phosphatidylserine in an accessible manner.

Annexines are a group of homologous proteins, from 35 to 45 k daltons, which are found in all mammals at different stages of development, as well as in other vertebrates such as arthropods, slime molds (26), yeasts, sponges, fungi, protozoa, plants and bacteria (27, 28). All mammalian cells, with the exception of erythrocytes, produce an annexine like annexine V. The structure of annexines and their properties are described in reviews (28, 29). These proteins have been sequenced and some of them are available as recombinant proteins (27). As set out above, cell membranes which have been damaged by a mechanism of some kind exhibit an increased capacity for binding annexines; this can be observed, for example, by comparing fresh erythrocytes with erythrocytes which have been subjected to a relatively long storage period. Insofar as this increase in capacity for bonding to annexine is the reflection of an anomaly, the measurement of the erythrocytes' capacity for coupling to annexine is found to be an important tool for the control of quality of the blood to be employed in blood transfusions.

Selection of blood for transfusion is done essentially using three criteria: the immunological compatibility of the donor and of the receiver, the absence of viral or parasitic contamination, and the absence of pathology in the donor. Suitable tests have been developed for verifying blood groups and possible viral or parasitic contaminations; the donor's state of health is evaluated simply by interrogation. It is of interest, however, to note that there is nothing in existence for controlling the degradation of the blood during its preservation, it being known that individual bloods can age at different rates. Another potential problem which can arise in the selection of the blood for transfusion is that of its control when a number of viruses or of pathogenic agents are still unknown and hence undetectable.

BRIEF SUMMARY OF THE INVENTION

A means, as proposed in the present invention, which has the advantage of being simple in use, makes it possible to discriminate the cells capable of coupling to annexines, in particular to annexine V, in the presence of calcium and exhibiting a perturbed membrane state, from normal cells in the mixture, and to determine their significance.

The present invention is an improved process for obtaining magnetic particles complexed with DMSA, forming ferrofluids called FFSH, the said ferrofluids being capable of being directly or indirectly coupled via covalent bonds to an effector making it possible to form FFSH-effector covalent complexes, the said process including the following additional stages in relation to the process described in French patent 2 662 539:

a) the FFSS, which consist of particles associated with the oxidation products of DMSA, are centrifuged before peptization of the flocculate formed when the ligand is added, b) the FFSS are next reduced by addition of dithiothreitol (DTT), which cuts the disulfide bridges and regenerates the DMSA, at basic pH, to form FFSH, c) the excess DTT is removed by flocculation of the FFSH at pH 2, the FFSH retained on a magnet being subsequently washed and resuspended in a neutral buffer, for example a PBS buffer.

The invention also relates to the process for obtaining DMSA-substituted magnetic particles (FFD) coupled covalently to an effector, and which includes the following stages:

a) Obtaining effectors exhibiting accessible thiol groups:

For the effector to be able to form covalent bonds with the thiol groups of the FFSS or of the FFSH, it must itself comprise thiol groups. Either the macromolecule itself comprises these said residues, or they are generated covalently by coupling to a difunctional reactant, which reactant itself must have these residues capable of reacting with the SH groups of the DMSA and a second reactive functional group capable of forming covalent bonds with the effector itself. A difunctional reactant which could be employed in this context is SPDP, which, besides a bond with a thiol group, is capable of forming a bond with primary amines; however, it is also possible to mention N-succinimidyl S-acetylthioacetate (SATA), succinimidyl bromoacetate or carboxydiimide, maleimides and the alkyl or aryl sulfonyl (tresyl, tosyl, and the like) chlorine-containing derivatives. The difunctional reactant, for example SPDP, is added to the effector in an anhydrous solvent (for example 1-methyl-2-pyrrolidone) and incubated for 2 hours at ambient temperature. The excess SPDP is removed by filtration or gel or by dialysis.

b) Coupling of the effector to FFSH: The effector exhibiting groups that can act with thiols either directly or indirectly by coupling with the difunctional reactant in the conditions described above is incubated in the presence of ferrofluids treated with DMSA and is reduced with DTT (FFSH) according to the process described above, thus forming an effector-FFSH covalent complex; a covalent complex is intended to mean that the covalency resides in the bond at the thiol groups, by formation of S—S bridges between the SH residues of the DMSA and the SH or sulfonic ester residues of the effector which is natural or substituted with the difunctional reactant; it may happen that thiol or other groups of the FFSH have not reacted in the preceding stages and, where applicable, these groups are masked by a saturation treatment with serum albumin which, after formation of the effector-FFSH complex (or those bonding the effector to the particles via another difunctional agent) makes them incapable of reacting with another reactant.

The effector-FFSH covalent complexes obtained (or those bonding the effector to the particles via another difunctional agent) are thus capable of forming affinity complexes with receptors or halves of affinity pairs capable of coupling to the effector, and the magnetic property of these complexes can be employed for discriminating, measuring and/or separating the effectors-FFSH which have reacted from those which have not reacted.

Such a separation is particularly advantageous when it is desired to separate categories of cells which differ in the nature of a receptor at the surface of the latter; this is because the existing separation methods are often traumatizing for the cells and the separations which can be applied to macromolecules, especially affinity chromatographs, are of little practical use for cell separations. A person skilled in the art knows in which case it is particularly advantageous to separate a particular category of cells in a complex mixture; the most striking examples which may be mentioned are the bone marrow strain cells for treating ex vivo and reinjecting them into patients in order to treat them using gene therapy, or else some categories of lymphocytes, to harvest the platelets which have not been activated and, more generally, any cells which it is desired to separate or eliminate, for example following a viral infection in order subsequently to reinject the cell "pool" in a homologous or autologous manner into individuals.

With this in mind, there is a category of cells which it is extremely difficult to discriminate: these are erythrocytes or red corpuscles which originate from ill or infected individuals or else which have degraded following an excessively long conservation period in vitro. The control of quality of the red corpuscles or of corpuscle concentrates today remains a major problem of transfusion therapeutics, with a doubt continuing to exist with regard to the health quality of the red corpuscles which are injected into patients, insofar as an infection that is too recent cannot be detected by conventional means of diagnostics, as it is not possible to detect infections by unknown pathogens, and as it is not possible to allow oneself to prolong the storage of pouches of blood without the risk of damaging a certain number of blood cells.

It was stated above that the cell membranes and especially the cell membranes of the red corpuscles are damaged or perturbed as a result of various pathologies or of their aging, or even of interrupting the cooling line, such a perturbation giving the cells an ability to bond to annexines.

The invention also relates to a process for obtaining magnetic particles forming ferrofluids complexed with DMSA so as to be able to be coupled to an annexine. Thiol groups can be generated by covalent coupling of annexines to SPDP. In the process of the invention and in order to form FFSH-annexine complexes, called AnxFF, the relation between the FFDTT and the annexine-SPDP is between 30 and 120 µg and preferably between 30 and 60 µg per 100 ml of FFSH.

The invention also relates to ferrofluid particles complexed with DMSA and treated with DTT by a process as described above, and to ferrofluid particles coupled covalently through the intermediacy of disulfide bridges between the DMSA and the effectors, which complexes are obtained by the process described above. A preferred embodiment of these complexes is ferrofluid particles coupled to an annexine.

In what precedes and what follows we shall speak without discrimination of effector-FF and effector-FFSH particles, of FF or FFD-effector complexes and when the effector is an annexine or an active peptide derived from annexine like, for example, the N-acetyl-lipocortine i peptide derived from annexine I (30), of Anx FF; and in all cases they are complexed with DMSA and then treated with DTT according to the improvement of the invention and coupled with a difunctional agent.

The present invention also relates to the use of the effector-FFSH complexes obtained by the process described above, for the differentiation and/or for the separation of the compounds carrying a receptor for the said effector from those not carrying the said receptor. The receptor here is understood to mean a molecule or a macromolecule which can form an affinity complex with the effector, regardless of whether this molecule or macromolecule is free in a medium or incorporated into a complex structure, for example a membrane.

In a preferred use according to the invention the ligand is an annexine and the receptor of the ligand is phosphatidylserine (PS) or phosphatidyl-ethanolamine (PE), phospholipids capable, in the presence of $Ca^{2+}$, of bonding to the Anx FF complex after perturbation of the membrane structures; in this case the use according to the invention makes it possible to differentiate and/or to separate the cells exhibiting a state which is abnormal—and hence capable of bonding to Anx FF in the presence of calcium ions—from the healthy cells incapable of binding these particles.

In the use of the invention the particles of the Anx FF are between 3 and 30 nm and preferably between 5 and 15 nm in size.

As stated above, the control of the erythrocytes before a blood transfusion or an injection of a corpuscle residue continues to present a problem of health safety of the said cells. One use of the particles according to the invention makes it possible to palliate the deficiency which existed hitherto: in a whole blood or in a corpuscle concentrate it is today possible to envisage detecting the presence of erythrocytes exhibiting an abnormal physiological state due to an excessive aging or being the reflection of a person's pathological state and, according to what is desired, to separate these abnormal cells from the healthy cells or simply to check a sample taken before a possible transfusion; the particles of the invention can, finally, be employed in a process of identification of a possible pathological state, as a preliminary stage before a more advanced identification by other means which are known to a person skilled in the art; this may be, for example, the presence of an inflammatory reaction, of autoimmune reactions or of a perturbation in the coagulation sequence. The annexine-ferrofluid (Anx FF) complexes can also be employed for a control of quality of the lymphocytes and of the platelets before these cells are employed, for example, for therapeutic purposes.

Recent observations (22) have shown that nitric oxide synthetase is inhibited by the phosphatidylserines secreted or exposed at the surface of the cells; in this context, the Anx FF particles of the invention can be employed for the manufacture of a medication intended for treating the immunity deficiencies induced by viruses or parasites.

The invention also relates to a method for differentiating and/or separating cells exhibiting an abnormal physiological or pathological state manifesting itself in the presence of a receptor for annexine, especially phosphatidylserine, at their surface, the said method including:

a) coupling of the Anx FF particles, obtained by a process described above and detailed in the examples below, to the cells in the presence of calcium ions;

b) separation of the cells coupled to the Anx FF from the uncoupled cells by the use of a magnetic field, c) counting or evaluation of the cells which have coupled to the Anx FF, d) the evaluation of the proportion of the healthy cells being carried out by the measurement of the relationship between the cells which have not reacted with the Anx FF and the total number of cells.

This method of the invention is applied preferably to erythrocytes; in this method the calcium ions are provided by $CaCl_2$ in a concentration of between 0.5 and 5 mM.

The core of this device for differentiation and/or separation is the magnetic property of the Anx FF particles; the invention also relates to a device permitting this differentiation and/or this separation, which would employ this property; the device according to the invention includes at least:

a) an electromagnet, b) a pump, c) a means for delivering the sample, d) a means for delivering the buffer containing $Ca^{++}$ ions, e) a means for delivering the washing buffer, f) valves making it possible to control the flows of the different fluids mentioned in c), d) and e).

The examples below and the various figures illustrate the invention without, however, any limitation thereof being implied.

DETAILED DESCRIPTION OF THE INVENTION

Example 1: Preparation of the DMSA Ferrofluids (FFSH)

The starting ferrofluid is a nitric ferrofluid synthesized according to the method of French patent 2 662 539. It consists of nanoparticles of maghemite $\gamma Fe_2O_3$ of a diameter of between 3 and 30 nm (mean diameter: 9 nm) charged positively at the surface in acidic medium (pH<6) or negatively in basic medium (pH>10).

The preparation of a sol which is stable at about pH 7–8 for producing a coupling in a homogenous liquid phase in conditions which are not denaturing for the proteins (in this case annexine) or other biological molecules is done by complexing of the surface irons using DMSA. The free thiol groups permit the formation of S—S bond with the SPDP bound beforehand to the protein via a peptide bond.

1st stage: 5 cm$^3$ of nitric ferrofluid ([Fe] =1 mol l$^{-1}$) are added to 250 cm$^3$ of a 10$^{-3}$ mol l$^{-1}$ solution of DMSA in degassed distilled water. The [DMSA]/[Fe] ratio is 0.05. Flocculation takes place and after 30 minutes the pH is near 4.5.

2nd stage: the excess DMSA is removed by centrifuging: 10 minutes at 3000 rev/min.

3rd stage: the flocculate is peptized with a 0.1 mol l$^{-1}$ sodium hydroxide solution to pH 11. A sol stable between pH 3 and 11 is formed. The volume is adjusted to 50 cm$^3$ and the pH to 7 with a dilute HCl solution. This DMSA-ferrofluid ([Fe] =10$^{-1}$ mol l$^{-1}$) is stable in time and serves as master solution for its subsequent applications.

4th stage: before coupling to the protein-SPDP, 1 cm$^3$ of the above ferrofluid is treated by the addition of 1 cm$^3$ of an aqueous solution of DTT at a concentration of 10$^{-2}$ mol l$^{-1}$ at about pH 9. It is left to incubate for 1 hour and the mixture is then flocculated by the addition of 0.1 mol l$^{-1}$ HCl to pH=2. After centrifuging for 10 minutes at 5000 rev/min the flocculate is peptized with a PBS solution (0.1 mol l$^{-1}$) and the pH is adjusted to 7.4. This precipitation-peptization sequence is recommended twice in order to remove completely the excess DTT and the DMSA possibly released during the cutting of the disulfide bridges. During the last peptization the volume of PBS is adapted to the desired concentration for the ferrofluid before its coupling by direct incubation with the protein-SPDP.

Example 2: Preparation of the Annexine-Ferrofluid Complex

1) The ferrofluid is treated with dimercaptosuccinic acid (DMSA) and reduced with dithiothreitol at pH 9.2 and at ordinary temperature (FFSH). After flocculation of FFSH at pH 2 and centrifuging, the supernatant containing the excess DTT is removed and the flocculate retained by a magnet is washed and then dispersed in a phosphate buffer (PBS). The thiol groups of the FFSH are determined using Ellman's reagent (5,5'-dithiobis(2-nitrobenzoic acid) (31), with minor modifications to remove the interference by the ferrofluid particles in the spectrophotometer reading.

2) An annexine, in this case recombinant annexine V, is reacted with SPDP in PBS medium, the SPDP being in excess in relation to the annexine (2.5 moles of SPDP per mole of annexine). The SPDP is dissolved in an anhydrous solvent, 1-methyl-2-pyrrolidone, and then added to the annexine in an aqueous medium; the mixture is left to incubate at ambient temperature. The annexine-SPDP is obtained and the excess SPDP is hydrolyzed spontaneously.

3) Various quantities of annexine SPDP are incubated with the FFSH for 2 hours at ambient temperature, the optimum ratio of the two components being determined experimentally, for example by measuring the change in the electrophoretic mobility of the particles in solution by employing the Doppler effect. In this case the electrophoretic mobility of the Anx FF complex is compared with that of the FFSH; another method is the determination of the enzymatic activity or of another functional property of the effector, such as its affinity for an antibody, or the ability to form an affinity complex with antibodies of a peroxidase/protein A complex immobilized on the particles, and the determination of the peroxidase activity. An optimum activity is obtained by the binding of 1.5 to 2 $\mu$g of annexine on 1 ml of FFSH, as the use of the above-mentioned methods has shown.

4) The DMSA which has not reacted with the effector and other potentially reactive sites on the ferrofluid particles are masked by saturation with 1% of BSA (for bovine serum albumin) in 50 mM of $NaHCO_3$ buffer and pH 9.6 to give the Anx FF. In some cases other proteins such as human serum albumin may be more appropriate. A particular attention is paid to avoid a flocculation resulting from an excess of saturation.

Example 3: Coupling of the Anx FF to the Cells

One method of producing the coupling of Anx FF to erythrocytes is to mix:

30 $\mu$l of a 30% suspension of erythrocytes,

30 $\mu$l of Anx FF,

6 $\mu$l of 125 mM $CaCl_2$, 7.5 $\mu$l of 4% BSA,

256 $\mu$l of buffer.

The reaction mixture is incubated for 30 min at 37° C. and then diluted with 6 ml of TRIS buffer to which has been added 0.1% BSA and 5 mM of DTT.

Example 4: Separation of the Cells Retained by Anx FF from the Unretained Cells

Figure 1:
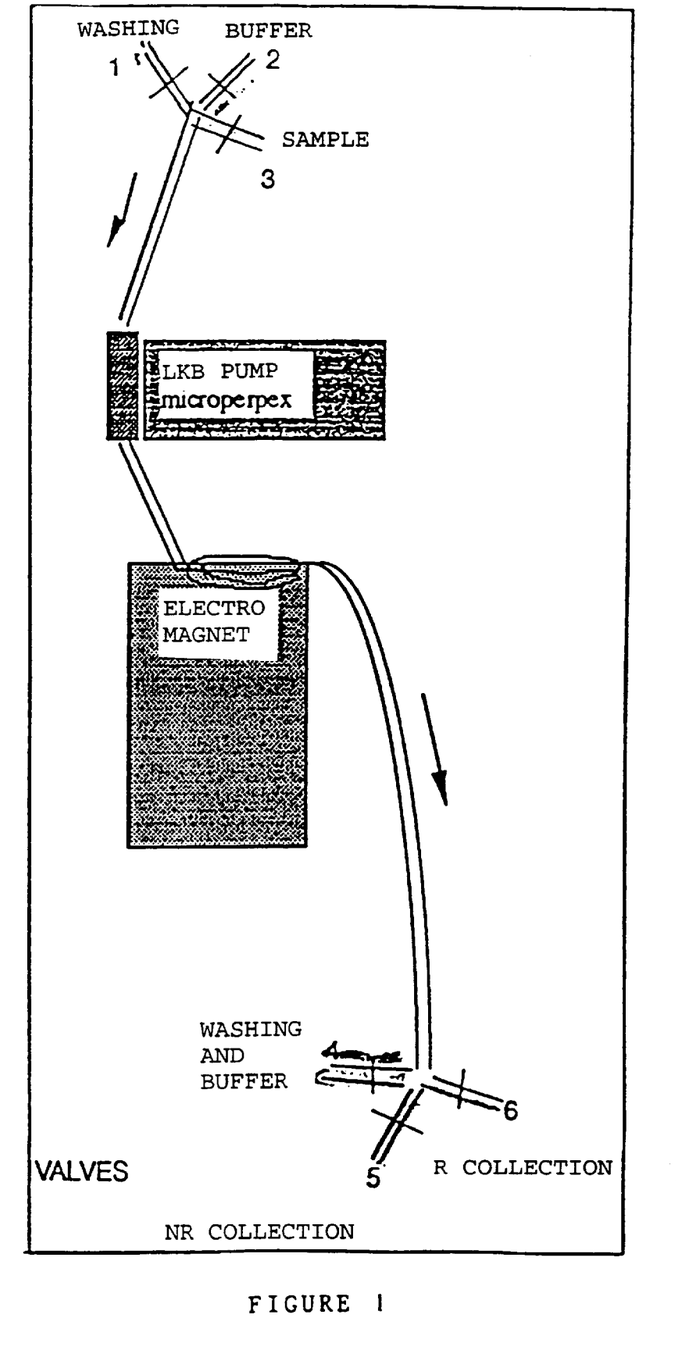
FIG. 1: automatic device for sorting red corpuscles or another target adopted using Anx FF.

This separation is carried out by an automatic apparatus, an example of which, given in FIG. 1 is the following: a tygon tube is placed in a magnetic field and connected to various storage containers via solenoid valves. The electromagnetic field is brought into action and the reaction mixture described in Example 3 above is, after an incubation at 37° C., introduced into the tube by actuating the appropriate valve and passes through the magnetic field at a rate of 120 ml per hour, and the effluent is collected.

A valve controlling a washing storage container is actuated and 15 ml of buffer pass through the tube. The washing buffer is harvested at the same level as the effluent consisting of cells not retained by the Anx FF.

The cells retained by the Anx FF are eluted from the tube by switching off the magnetic field and by harvesting the cells retained in 8 ml of buffer. The cells retained and not retained are concentrated by centrifuging at 3000 g for 7 min and at 4° C. and then counted before any eventual subsequent treatment or characterization. A quantification of the receptors with annexine in a cell population can be done by employing annexine tagged with iodine 125.

If reference is made to FIG. 1, during the first stage of washing with physiological water the valves 1 and 4 are open and the valves 2, 3, 5 and 6 are closed; the pump is at its maximum for 2 to 10 minutes and then stopped.

The buffer is next introduced through the same tube (valves 2 and 4 open). The sample of the concentrate is introduced with a flow rate of 160 ml/hour, valves 3 and 5 being open (1, 2, 4, 6 closed). The pump operates between 3 and 60 seconds and then stopped.

The fraction not retained in the presence of $CaCl_2$ buffer is next collected by passing the buffer at a rate of 160 ml per hour, valves 2 and 5 being open (1, 3, 4, 6 closed). The pump is in action for 2 to 10 minutes and then turned off.

The fraction retained is obtained after washing with physiological water, valves 1 and 6 being open (2, 3, 4, 5 closed), the electromagnet being switched off and the pump brought into action for 2 to 10 minutes.

A last washing with physiological water is performed by opening valves 1 and 4 (2, 3, 5, 6 closed) for 2 to 10 minutes.

COMPARATIVE RESULTS a) Effects of calcium ions.

Figure 2:
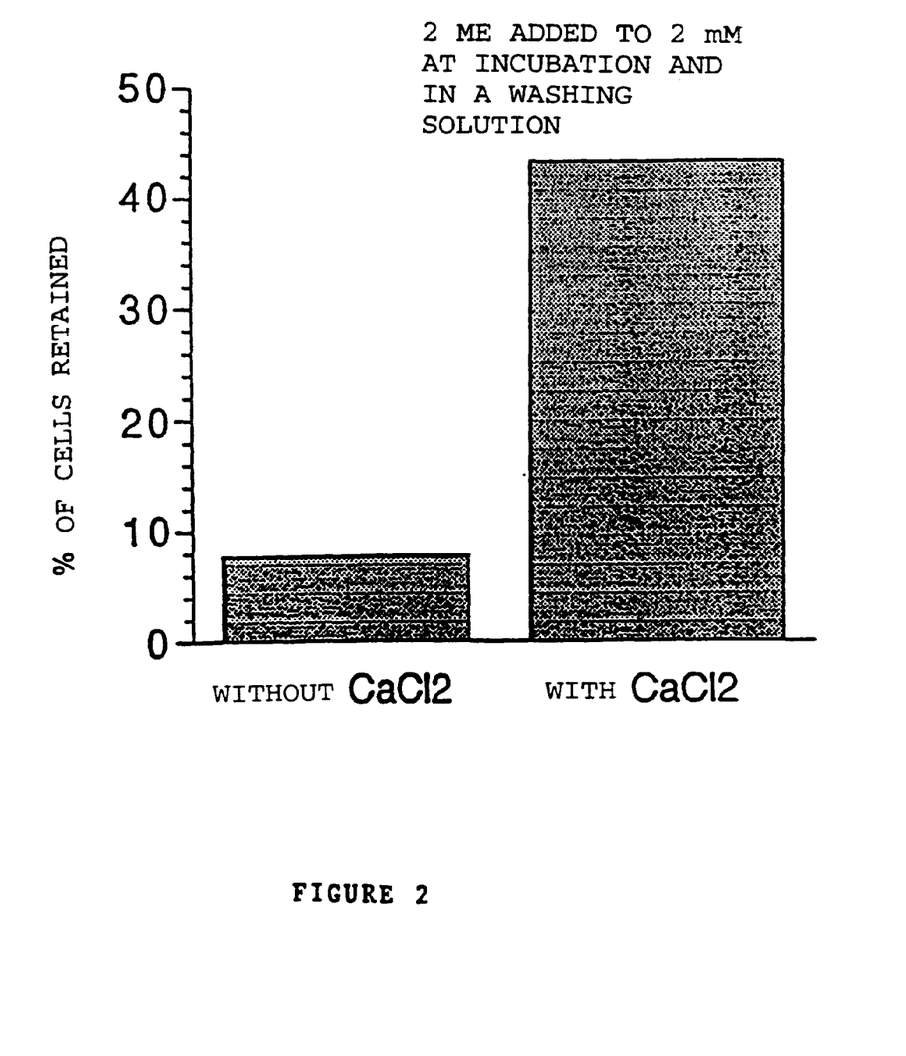
FIG. 2: influence of the $Ca^{2+}$ cations on the coupling of Anx FF with erythrocytes.
Figure 3:
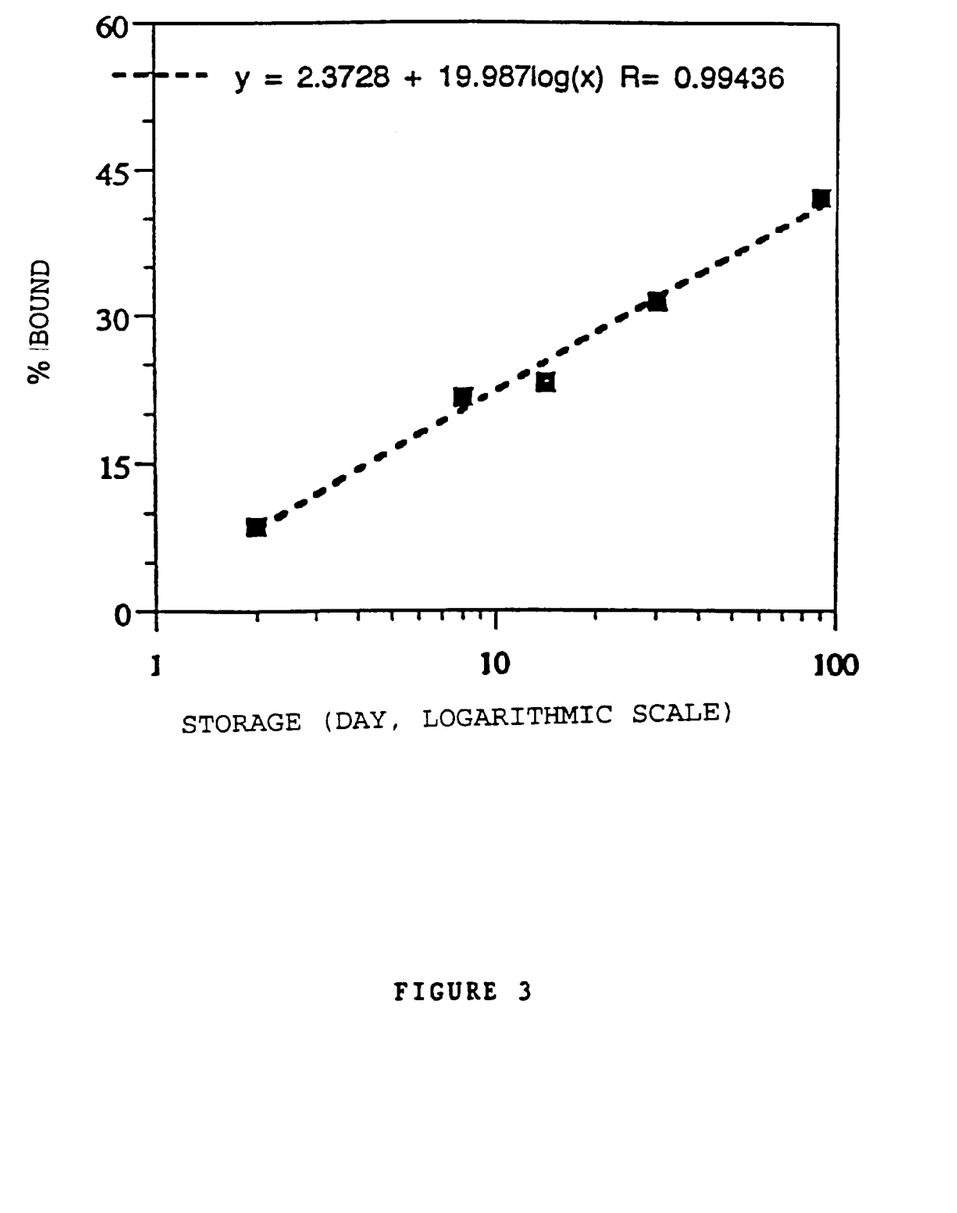
FIG. 3: change in the coupling of erythrocytes with Anx FF in the course of storage in vitro.

FIG. 2 shows the percentage of cells retained on the Anx FF particles as a function of the presence or absence of $CaCl_2$. It is seen that 44% of the cells are retained in the presence of calcium ions, whereas only 8% are retained in the absence of calcium ions.

b) Effect of the age of the erythrocytes,

FIG. 3 shows the percentage of erythrocytes bonded to Anx FF as a function of the time of in vitro storage of the red corpuscles. It is clear that this percentage increases logarithmically as a function of the storage time, indicating an increasing deterioration of the membranes of the said red corpuscles. One week of storage results in 22% of coupling, one month in 30% and three months in 42%.

In the mouse a storage of 24 hours already entails a coupling of 13%, whereas no bonding is observed with freshly collected blood.

c) Effect of the erythrocyte concentration on the separation of the erythrocyte-Anx FF complexes.

Figure 4:
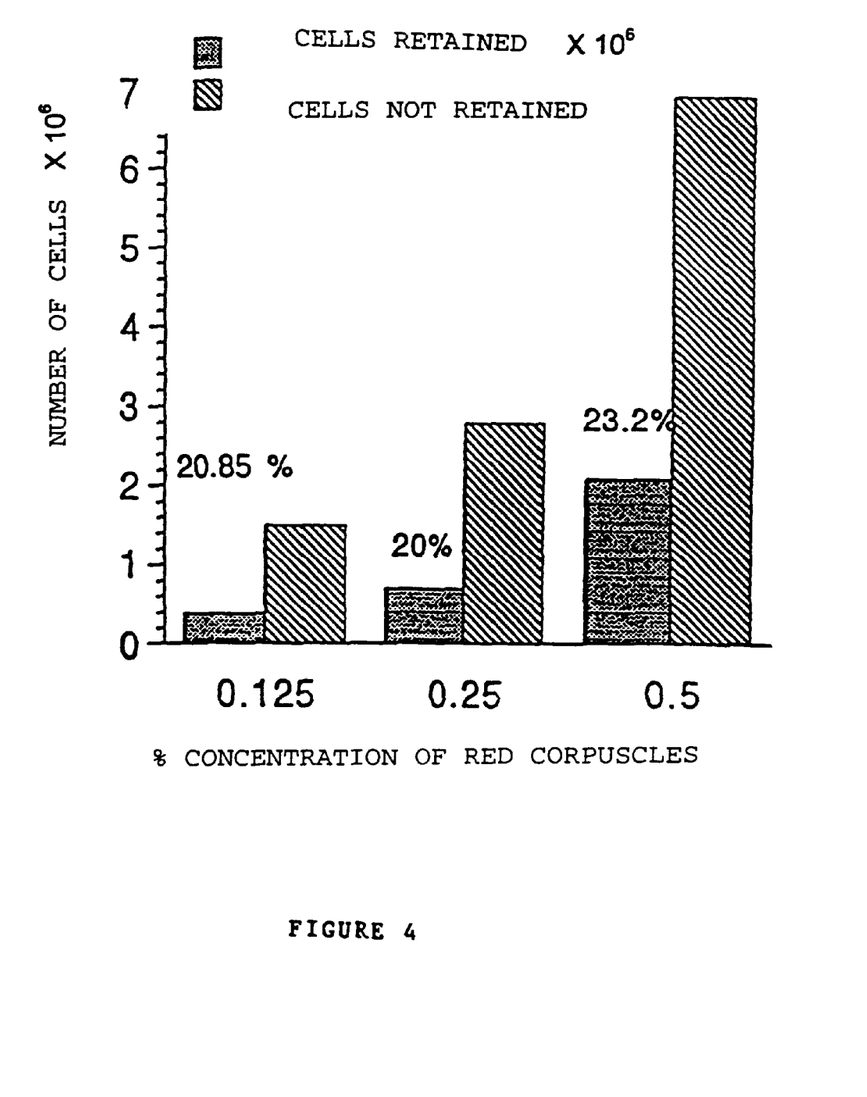
FIG. 4: degree of retention of the erythrocytes by Anx FF as a function of the number of cells employed in the test.

This effect is illustrated in FIG. 4, which shows that the result obtained is independent of the concentration of red corpuscles in the solution: in the conditions employed, between 20 and 24% of the cells are retained, whatever the concentration employed.

d) Effect of the various doses of annexine-FFSH on the retention of the erythrocytes.

Figure 5:
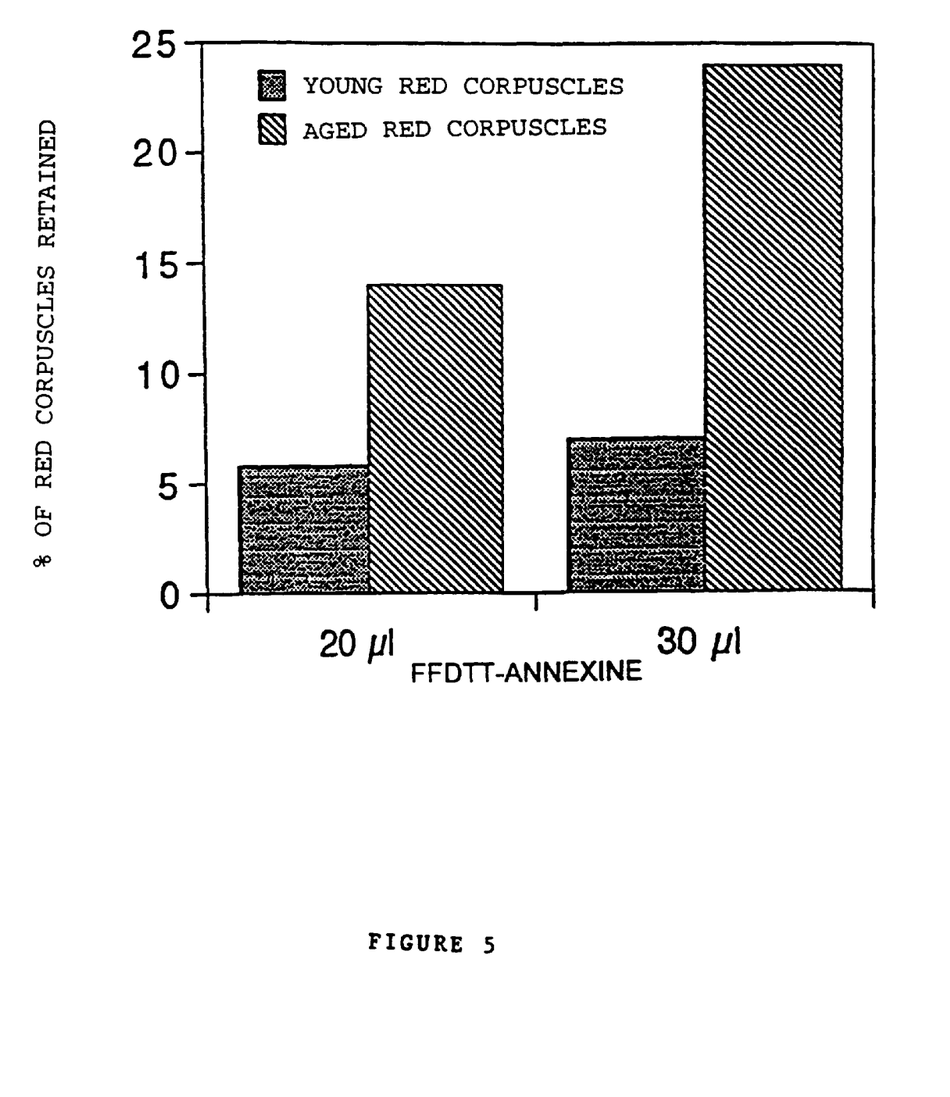
FIG. 5: degree of retention of the erythrocytes as a function of the quantity of Anx FF employed in the test.

FIG. 5 shows the percentage of red corpuscles retained on the Anx FF in the presence of 20 µl or 30 µl of annexine-FFSH. It is seen that 20 µl of Anx FF are sufficient to obtain a maximum retention starting with a young erythrocyte population, whereas 30 µl are needed for aged erythrocytes.

f) Relationship between the Anx FF coupling of the erythrocytes and the physiological or pathological state of these same red corpuscles.

The table below shows the results obtained individually on control samplings performed by the French Blood Agency.

| FBA control | Normal SR | Sickle cell anemia | High SR | Other pathologies |
|---|---|---|---|---|
| 19.60 | 21.73 | 50.00 | 36.94 | 49.76 |
| 0.00 | 16.75 | 49.00 | 36.37 | 63.00 |
| 14.80 | 19.56 | 64.00 | 51.26 | 63.00 |
| 12.00 | 27.59 | 35.00 | 54.49 | |
| 11.90 | 32.00 | 49.00 | 49.85 | |
| 18.00 | | 53.20 | 46.80 | |
| 0.00 | | | 65.70 | |
| 12.60 | | | 71.00 | |
| 14.00 | | | | |
| 5.90 | | | | |
| 12.00 | | | | |
| 10.00 | | | | |
| 8.70 | | | | |
| (*)10.7 ± 5.9 | 23.5 ± 6.2 | 50 ± 9.3 | 51.5 ± 12.3 | 58.6 ± 7.6 |

(*)Mean

The mean retention of the red corpuscles on the Anx FF is 10.7 plus or minus 5.9. The results given in the last four columns relate to blood samples of subjects who have attended medical analysis laboratories. The samples were assigned to us, the anonymity of the subjects being preserved. Only the sedimentation rate (SR) was known to us. Results given in the second column show a moderately raised degree of retention in subjects with normal SR whose pathology has remained unknown to us. The results given in the fifth column relate to subjects also with normal SR but exhibiting a markedly higher degree-of retention, in whose cases it was possible to identify the pathology after investigation: one case of carcinoma (the subject being under chemotherapy), one case of deforming rheumatism and one case of onset of rhinopharingitis. The results given in the third and fourth columns relate to blood samples with a high SR from subjects presenting a known (third column) or unknown pathology (fourth column). These results clearly indicate that an abnormally high percentage of retention on the Anx FF is the reflection of a physiological or pathological state which must cause the transfuser to reject the batch of red corpuscles for transfusion purposes.

REFERENCES (1) J. M. Lewis, E. T. Menz, F. E. Kenny, E. V. Groman, L. Josephson, U.S. Pat. No. 5,055,288 (1991)

(2) H. Pilgrimm, U.S. Pat. No. , 5,160,725 (1992) (30 E. V. Groman, L, Josephson, U.S. Pat. No. , 5,248,492 (1993)

(4) Giaever, U.S. Pat. No. , 4,115,535 (1978)

(5) K. J. Widder, EU Patent, 0,016,552 A1, (1980)

(6) R. S. Molday, U.S. Pat. No. , 4,452,773, (1984)

(7) R. A. Whitehead, M. S. Chagnon, E. V. Groman, L. Josephson, U.S. Pat. No. 4,695,392 (1987)

(8) C. S. Owen, J. C. Silvia, L. D'Angelo, P. A. Lierti, U.S. Pat. No. , 4,795,698 (1989)

(9) C. H. Wang, D. O. Shah, Int Patent, WO 91/09141, (1991)

(10) R. T. Gordon, U.S. Pat. No. , 4,735,796, (1988)

(11) M. Hasegawa, S. Hokkoku, U.S. Pat. No. , 4,101,435, (1978)

(12) U. Schroder, K. Mosbachhhh, U.S. Pat. No. , 4,501, 726, (1985)

(13) M. Okada, Y. Ashihara, A. Yano, M. Oishi, K. Yoshioka, T. Nakamura, Eur. Patent, 0 420 186 A2, (1990)

(14) R. Massart, V. Cabuil-Marchal, J. M. Fruchart, J. Roger, J. N. Pons, M. Carpentier, S. Neveu, R. Brossel, T. Bouchami, A. Bee-Debras, Fr Patent, 90 06 484 (1990)

(15) J. Carlsson et al., Biochem J., 173,723, (1978)

(16) V. A. Fadok, D. R. Voelker, P. A. Campbell, J. J. Cohen, D. L. Bratton, P. M. Henson, J. Immunol., 148,2207, (1992)

(17) J. Matsuda, N. Saitoh, K. Gohchi, M. Gotoh, M. Tsukamoto, Amer. J. Hematol, 47,56? (1994)

(18) B. Lubin, D. Chiu, J. Bastacky, B. Roelofsen, L. L. M. Van Deenen, J. Clin, Invest, 67, 1643 (1981)

(19) J. F. Wright, A. Kurosky, S. Wasiiii, Biochem, Biophys. Res Comm., 198,983, (1994)

(20) M. Otto, A. Gunther, H. Fan, O. Rick, R. T. C. Huang, FEBS lett, 356,125 (1994)

(21) A R Neurath, N Strick, Virol., 204,475 (1994)

(22) H. Cesar Calderon, Z. H. Huang, D. A. Ggae, E. M. Sotomatoyor, D. M. Lopez, J. Exp. Med., 180,945, (1994)

(23) J. F. Tait, D. Gibson, J. Lab, Clin. Med., 123,741, (1994)

(24) A. J. Schroit, J. W. Masden, Y. Tanaka, J. Biol. Chem, 260, 5131, (1985)

(25) L. McEvoy, p; Williamson, R. A. Schlegel, Proc. Natl. Acad. Sci. (US), 83,3311, (1986)

(26) C. E. Creutz, J. Redick, Mol. Biol. of the Cell, 5,324a (1994)

(27) P. Raynal, H. B. Polard, Biochim. Biophys. Acta, 1197,63, (1994)

(28) P. F. Devaux, Ann. Rev. Biophys. Biomol. Struct, 21,417, (1992)

(29) P. D. Smith, S. E. Moss, trends in Genet., 10,241, (1994)

(30) M. Perretti and R. J. Flower, Pharmacol. Res., 30,53 (1994)

(31) G. L. Ellman, Arch. Biochem. Biophys., 82, 70 (1959)

What is claimed is:

1. A method for obtaining ferrofluid-forming magnetic particles substituted with dimercaptosuccinic acid (DMSA) which are capable of being covalently coupled to an effector, the method comprising combining DMSA with ferrofluid-forming magnetic particles, thereby producing ferrofluid-forming particles having disulfide bonds (FFSS), and reducing the disulfide bonds of the FFSS at a basic pH to form ferrofluid-forming magnetic particles substituted with DMSA having reduced thiol groups (FFSH).

2. The method of claim 1, wherein flocculation of the FFSS takes place, and further comprising
   (i) centrifuging the flocculated FFSS, and peptizing the flocculated FFSS particles in a basic solution, and after forming the FFSH,
   (ii) flocculating the FFSH in an acidic solution, and washing and re-suspending the FFSH in aqueous buffer.

3. The method of claim 1, further comprising covalently binding an effector to the FFSH to form a covalent effector-FFSH complex wherein the covalent bond is an S—S, C—S, C—C, or C—N bond.

4. The method of claim 3, further comprising covalently attaching a difunctional reactant comprising at least one functional group to an effector to produce an effector capable of covalently binding to FFSH.

5. The method of claim 3, further comprising, following formation of an effector-FFSH complex, masking unreacted reactive groups of the FFSH by a saturation treatment with serum albumin.

6. A composition comprising a ferrofluid-forming magnetic particle complexed with DMSA having reduced thiol groups FFSH.

7. The composition according to claim 6, wherein the FFSH is covalently coupled to an effector.

8. The composition according to claim 7, wherein the effector has a covalently bound difunctional reactant through which it is attached to the FFSH.

9. The composition of claim 7, wherein the effector that is coupled to FFSH is an annexine.

10. The composition according to claim 7 wherein the molar relationship between the FFSH and the effector is between 1:1 and 3:1.

11. A method for identifying molecules or cells having a ligand that forms an affinity complex with an effector coupled to FFSH, the method comprising:
   a) mixing the molecules or cells with the effector coupled to FFSH; and
   b) subjecting the mixture to a magnetic field to separate the molecules or cells having said ligand from the molecules or cells that do not have such a ligand.

12. The method of claim 11, further comprising detecting the molecules or cells which bind to the effector-coupled FFSH particles.

13. The method of claim 12, further comprising identifying cells presenting an abnormal or pathological physiological state associated with the presence in cellular outer membranes of an anionic phospholipid that forms an affinity complex with annexine as the effector coupled to FFSH, the method comprising:
   a) complexing cells, in the presence of calcium ions, with annexine-FFSH;
   b) subjecting the complex of cells and annexine-FFSH to a magnetic field and washing, so as to separate cells bound annexine-FFSH from cells not bound to annexine-FFSH; and
   c) determining the fraction of the cells bound to annexine-FFSH.

14. The method of claim 13 wherein the anionic phospholipid in the cellular outer membranes that is associated with an abnormal or pathological state is phosphatidylserine or phosphatidylethanolamine.

15. The method of claim 13 wherein the cells are erythrocytes from an individual, and wherein identification of an abnormally high fraction of said erythrocytes having said anionic phospholipid in their outer membranes:
   a) indicates the presence of erythrocytes presenting an abnormal physiological state; and/or
   b) permits determining and controlling the state of health of blood cells in a blood sample before transfusion; and/or
   c) is indicative of a pathological condition in the individual from whom the erythrocytes were obtained.

16. The method of claim 13 wherein the annexine-FFSH particles have a diameter that is between 3 and 30 nm.

17. The method of claim 13 wherein the calcium ions present in step a) are provided as $CaCl_2$ in a concentration between 0.5 and 5 mM.

18. A device for identifying or separating compounds or cells having a ligand that forms an affinity complex with an effector coupled to a ferrofluid-forming magnetic particle substituted with DMSA having reduced thiol groups according to the method of claim 11, the device comprising:
   a) an electromagnet;
   b) one or more channels able to selectively direct the flow of sample, buffer, and wash solutions through the magnetic field of the electromagnet to effect separation into retained and non-retained fractions;
   c) a pump connected to said channels; and
   d) one or more apertures from which the retained and non-retained fractions are collected.

19. A device for identifying or separating from a sample solution compounds or cells having a ligand that forms an affinity complex with an effector coupled to a ferrofluid-forming magnetic particle substituted with DMSA having reduced thiol groups according to the method of claim 11, the device comprising:
   a) a means for subjecting the sample solution to a magnetic field;
   b) a means for directing the sample solution through said magnetic field to separate the compounds or cells having the ligand; and
   c) a means for collecting the compounds or cells having the ligand separately from compounds or cells not having the ligand.

* * * * *